United States Patent
Endo et al.

(10) Patent No.: US 9,179,893 B2
(45) Date of Patent: Nov. 10, 2015

(54) IMAGE PROCESSING APPARATUS, IMAGE PROCESSING METHOD, IMAGE PROCESSING SYSTEM, AND PROGRAM

(75) Inventors: Takaaki Endo, Urayasu (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 273 days.

(21) Appl. No.: 13/516,623

(22) PCT Filed: Oct. 6, 2010

(86) PCT No.: PCT/JP2010/005983
§ 371 (c)(1),
(2), (4) Date: Jun. 15, 2012

(87) PCT Pub. No.: WO2011/074162
PCT Pub. Date: Jun. 23, 2011

(65) Prior Publication Data
US 2012/0249549 A1 Oct. 4, 2012

(30) Foreign Application Priority Data
Dec. 18, 2009 (JP) .................................. 2009-288455

(51) Int. Cl.
G06T 15/00 (2011.01)
G06T 15/20 (2011.01)
A61B 8/08 (2006.01)
G06T 19/00 (2011.01)
A61B 8/00 (2006.01)

(52) U.S. Cl.
CPC ............... *A61B 8/483* (2013.01); *A61B 8/4416* (2013.01); *G06T 19/00* (2013.01); *A61B 8/00* (2013.01); *G06T 2219/008* (2013.01); *G06T 2219/2004* (2013.01)

(58) Field of Classification Search
CPC combination set(s) only.
See application file for complete search history.

(56) References Cited

U.S. PATENT DOCUMENTS

| 2004/0210138 A1* | 10/2004 | Murashita et al. ............. 600/443 |
| 2007/0010743 A1* | 1/2007 | Arai .............................. 600/443 |
| 2009/0220136 A1* | 9/2009 | Bova et al. ..................... 382/131 |

FOREIGN PATENT DOCUMENTS

| JP | 2005-169070 A | 6/2005 |
| JP | 2006-20937 A | 1/2006 |
| JP | 2008-188417 A | 8/2008 |
| JP | 2009-112468 A | 5/2009 |
| JP | 2009-519077 A | 5/2009 |

* cited by examiner

*Primary Examiner* — Jason Repko
*Assistant Examiner* — Leon T Cain, II
(74) *Attorney, Agent, or Firm* — Canon USA Inc. IP Division

(57) ABSTRACT

An image processing apparatus includes a display control unit configured to display cross-sectional images based on planes passing through positions designated for a plurality of items of three-dimensional image data; and a change unit configured to cooperatively rotate the planes around the designated positions and to change the cross-sectional images to be displayed.

17 Claims, 7 Drawing Sheets

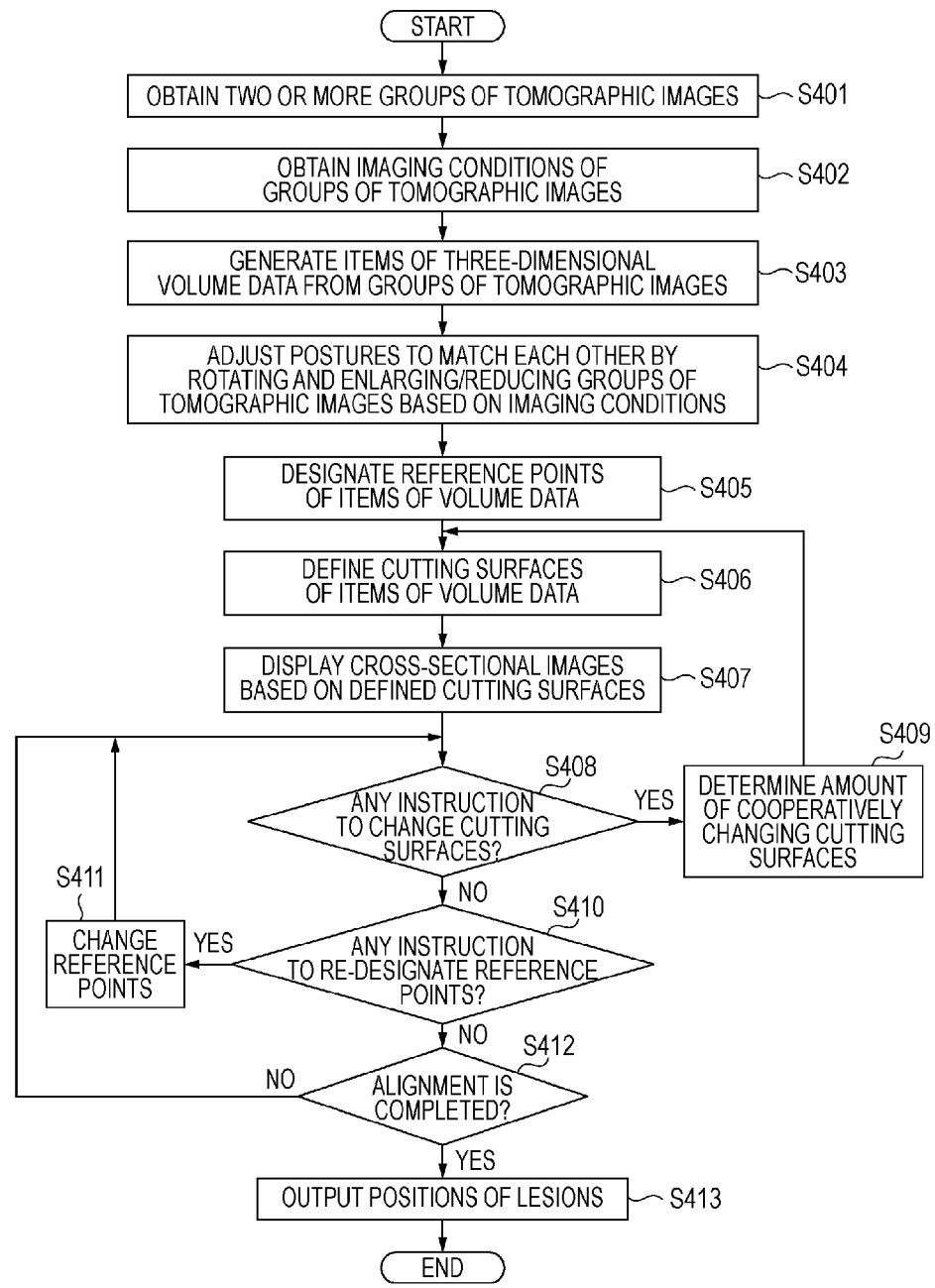

IMAGE PROCESSING APPARATUS, IMAGE PROCESSING METHOD, IMAGE PROCESSING SYSTEM, AND PROGRAM

CROSS REFERENCE TO RELATED APPLICATIONS

This application is a National Stage filing of International Application No. PCT/JP2010/005983 filed Oct. 6, 2010, which claims priority from Japanese Patent Application No. 2009-288455 filed Dec. 18, 2009, the disclosures of each of which are hereby incorporated by reference herein in their entirety.

TECHNICAL FIELD

The present invention relates to an image processing apparatus, an image processing method, and an image processing system for aligning a plurality of items of three-dimensional image data, and a program for causing a computer to perform image processing.

BACKGROUND ART

In the medical field in recent years, image diagnosis using a three-dimensional image including a group of tomographic images that visualize the interior of a subject has been conducted. Medical image collecting apparatuses (modalities) that capture such a three-dimensional image include ultrasonic imaging apparatuses, magnetic resonance imaging apparatuses (MRI imaging apparatuses), X-ray computer tomography imaging apparatuses (X-ray CT imaging apparatuses), and the like.

Diagnosis using a plurality of images captured using these modalities is conceivable. For example, diagnosis can be conducted by comparing three-dimensional images obtained by capturing images of the same portion using different modalities. Accordingly, the state of a lesion can be accurately diagnosed using advantages of the individual modalities, compared with the case where an image captured using a single modality is used. In another example, changes over time such as the progression of a lesion or the state of a deformity can be checked by comparing a plurality of items of three-dimensional data obtained by intermittently capturing images of a subject using a single modality.

In order to combine and use these plurality of items of three-dimensional image data, the plurality of items of three-dimensional image data are aligned by associating designated points such as lesions in the plurality of items of three-dimensional image data. In particular, because precise alignment is necessary in images used for diagnosis, the technique of performing an alignment checking operation also becomes necessary.

Patent Literature 1 discloses the technique of displaying a fixed two-dimensional cross-sectional image including a remarkable lesion in one of two items of three-dimensional image data, changing the cross-section of the other item of three-dimensional image data in accordance with a user operation, and displaying a cross-sectional image based on this cross-section. Accordingly, whether alignment is achieved can be checked by moving one of the two cross-sections.

CITATION LIST

Patent Literature

PTL 1: Japanese Patent Laid-Open No. 2005-169070

SUMMARY OF INVENTION

Technical Problem

However, as in the background art, when one of two two-dimensional cross-sectional images is fixed, it is difficult to perform alignment when a corresponding feature is difficult to be found from the fixed cross-sectional image. Even when a feature portion is included in the fixed cross-sectional image, the three-dimensional shape of the feature portion cannot be specified from the two-dimensional cross-sectional image. Thus, it is difficult to check whether the two two-dimensional cross-sectional images precisely correspond to each other.

Solution to Problem

Accordingly, an image processing apparatus according to an aspect of the present invention includes the following elements: a display control unit configured to display cross-sectional images based on planes passing through positions designated for a plurality of items of three-dimensional image data; and a change unit configured to cooperatively rotate the planes around the designated positions and to change the cross-sectional images to be displayed.

Advantageous Effects of Invention

In the present invention, feature portions of cross-sectional images around designated positions can be compared by cooperatively moving cross-sections, and changes of the feature portions in accordance with changes of the cross-sections can be compared. Accordingly, whether three-dimensional images are precisely aligned can be accurately checked.

BRIEF DESCRIPTION OF DRAWINGS

FIG. 4 is a flowchart illustrating the overview of a process executed by the image processing apparatus.

DESCRIPTION OF EMBODIMENTS

First Embodiment

An image processing apparatus according to an embodiment defines cutting surfaces of two different items of three-dimensional image data, and displays cross-sectional images based on these cutting surfaces. Here, the cutting surfaces are cooperatively changed, and the cross-sectional images based on the cutting surfaces are displayed. Looking at the two cross-sectional images, a user compares feature values and changes of features as a result of changing the cutting surfaces, thereby checking whether the different items of three-dimensional image data are aligned. Also, designations of the positions of corresponding points are updated in accordance with a user input, and the user performs alignment while browsing images. Hereinafter, a configuration and a process in the present embodiment will be described using FIGS. 1 to 4.

Figure 1:
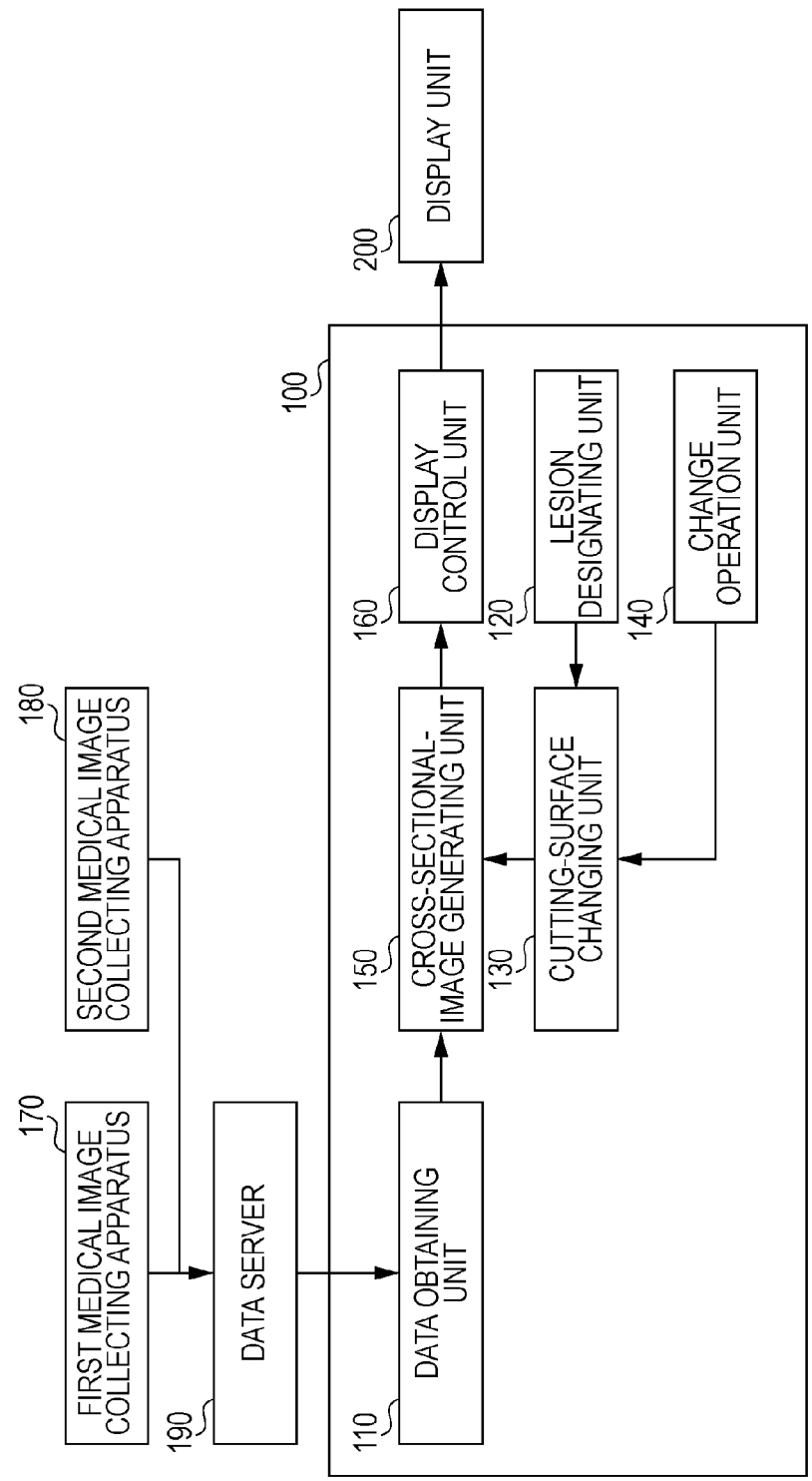
FIG. 1 is a block diagram of an image processing system according to a first embodiment.

FIG. 1 illustrates the configuration of an image processing system according to a first embodiment. An image processing apparatus 100 includes, for example, a data obtaining unit 110, a lesion designating unit 120, a cutting-surface changing unit 130, a change operation unit 140, a cross-sectional-image generating unit 150, and a display control unit 160, which include dedicated circuits. Also, the image processing apparatus 100 is connected to a first medical image collecting apparatus 170 and a second medical image collecting apparatus 180 via a data server 190. An MRI imaging apparatus serving as the first medical image collecting apparatus 170 captures images of a subject and obtains a first item of three-dimensional image data. An ultrasonic imaging apparatus serving as the second medical image collecting apparatus 180 captures images of the subject and obtains a second item of three-dimensional image data. These items of image data are stored in the data server 190. Image collecting apparatuses (modalities) include MRI imaging apparatuses, ultrasonic imaging apparatuses, X-ray CT imaging apparatuses, and the like. In the present embodiment, the first medical image collecting apparatus 170 is an MRI apparatus, and the second medical image collecting apparatus 180 is an ultrasonic imaging apparatus.

The first item of three-dimensional image data held by the data server 190 is a group of tomographic images obtained by capturing, in advance, images of the subject using the MRI apparatus. It is assumed that the position and posture of the subject included in the individual MRI tomographic images constituting the first item of three-dimensional image data are converted into a reference coordinate system (a coordinate system in space based on the subject) and held in the data server 190. The first item of three-dimensional image data represented in the reference coordinate system is input to the image processing apparatus 100 via the data obtaining unit 110.

The posture is the state of rotation or inclination represented by three angle components, namely, roll, pitch, yaw, in a three-dimensional space.

In contrast, the second item of three-dimensional image data held by the data server 190 is a group of tomographic images obtained by capturing, in advance, images of the subject using the ultrasonic imaging apparatus. A three-dimensional sensor is attached to an ultrasonic probe that is an image capturing unit (not illustrated) of the ultrasonic imaging apparatus. The three-dimensional sensor includes, for example, FASTRAK of Polhemus in the United States. With the three-dimensional sensor, the position and inclination in the reference coordinate system of the ultrasonic probe can be obtained. Accordingly, the position and posture of the ultrasonic tomographic images when the images of the subject are captured can be obtained. This information of the position and posture is used when three-dimensional volume data is generated by aligning a plurality of ultrasonic images obtained by the ultrasonic probe. The volume data is data storing a luminance value in each of voxels constituting a three-dimensional voxel mesh.

The data obtaining unit 110 obtains the first and second items of three-dimensional image data input to the image processing apparatus 100, and outputs the first and second items of three-dimensional image data to the lesion designating unit 120. Also, the data obtaining unit 110 reconstructs first and second items of three-dimensional volume data from the first and second items of three-dimensional image data. The data obtaining unit 110 outputs these items of volume data to the cross-sectional-image generating unit 150. Since the positions and postures of the tomographic images constituting the first and second items of three-dimensional image data are obtained in the reference coordinate system, the data obtaining unit 110 uses these items of data and reconstructs two items of volume data in the common reference coordinate system, thereby adjusting the postures. That is, the positions and postures of the two items of volume data are roughly aligned, excluding the influence of an error of the three-dimensional sensor and deformation of the subject. By displaying images in which the postures are aligned, a user's effort of aligning the postures can be alleviated.

The first and second items of volume data are held in a storage unit (not illustrated) in the image processing apparatus 100.

The lesion designating unit 120 obtains the first and second items of three-dimensional image data that are output of the data obtaining unit 110. The lesion designating unit 120 designates, as a first designation point, the position of a portion regarded as a lesion (remarkable lesion) in the first item of three-dimensional image data. Similarly, the lesion designating unit 120 designates, as a second designation point, the position of a portion regarded as a lesion (corresponding lesion) in the second item of three-dimensional image data, which corresponds to the remarkable lesion. These designations are intended to designate the initial positions and are not necessary to be accurate. The lesion designating unit 120 preferably designates lesions that correspond to each other. Because lesions are characteristic regions in images, the images can be more easily aligned later. By using a remarkable lesion as the center of alignment, the remarkable lesion can be highly precisely aligned, thereby improving the accuracy of diagnosis. Alternatively, a portion different from a lesion may be designated as a remarkable point.

The cutting-surface changing unit 130 determines cutting surfaces of the individual items of volume data including the designation points designated by the lesion designating unit 120. The cutting surfaces are defined for the first and second items of volume data. The inclinations of the cutting surfaces with respect to a patient are preferably made equal. Since the coordinate systems in the two items of volume data are made equal by the data obtaining unit 110, it is easy to roughly make the inclinations of the cutting surfaces equal. Here, even when the designation points do not accurately correspond to the position of the actual lesion, a user can perform re-designations while looking at images.

The change operation unit 140 receives an input entered by operating a mouse by a user. Based on the entered input information received by the change operation unit 140, the cutting-surface changing unit 130 cooperatively changes the cutting surfaces of the two items of volume data. A process thereof will be described in detail later.

The cross-sectional-image generating unit 150 generates (obtains) cross-sectional images of the first and second items of volume data based on the cutting surfaces determined or changed by the cutting-surface changing unit 130.

The display control unit 160 generates data for display in which the generated two cross-sectional images are arranged adjacent to each other, and controls a display unit 200 to display the data for display.

When a user checks the two cross-sectional images displayed by the display control unit 160 and determines that the positions designated in these items of volume data match each other, if the user inputs the designated positions as corresponding points, information of these corresponding points is stored in the storage unit, thereby completing the alignment.

Figure 2:
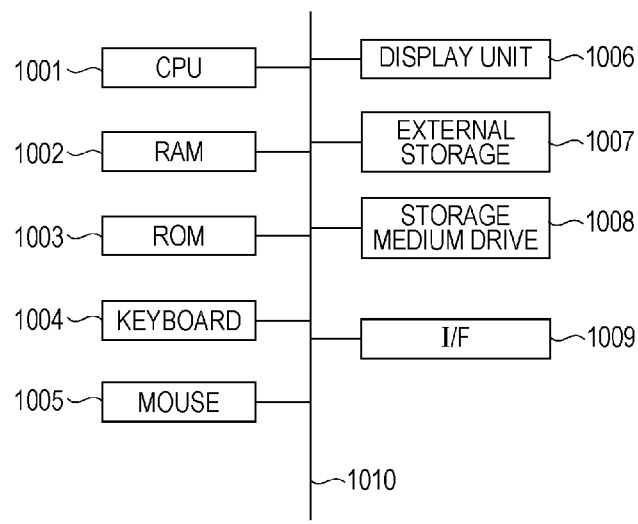
FIG. 2 is a diagram illustrating an embodiment of the hardware configuration of an image processing apparatus.

FIG. 2 is a diagram illustrating the basic configuration of a computer for realizing the functions of the units illustrated in FIG. 1 by executing software.

A CPU 1001 controls the entire computer using data and a program that are stored in a RAM 1002 or a ROM 1003, that realize the functions of the units illustrated in FIG. 1, and that realize a process illustrated in the flowchart of FIG. 4. The CPU 1001 controls execution of software in the units and realizes the functions of the units.

The RAM 1002 includes an area that temporarily stores a program and data loaded from an external storage 1007 or a storage medium drive 1008, and a work area necessary for the CPU 1001 to perform various processes.

The ROM 1003 generally stores a computer program and setting data. A keyboard 1004 and a mouse 1005 are input devices. Using these input devices, a user can input various instructions to the CPU 1001.

A display unit 1006 includes a CRT or a liquid crystal display. The display unit 200 in FIG. 1 corresponds to the display unit 1006. Besides cross-sectional images generated by the cross-sectional-image generating unit 150, the display unit 1006 can display a message or GUI to be displayed for image processing.

The external storage 1007 is a device that functions as a large-capacity information storage device such as a hard disk drive. An operating system (OS) and a program executed by the CPU 1001 are saved in the external storage 1007. In the description of the present embodiment, information described as being known is saved in the external storage 1007 and is loaded, as occasion calls, to the RAM 1002.

In accordance with an instruction from the CPU 1001, the storage medium drive 1008 reads a program and data stored in a storage medium such as a CD-ROM or a DVD-ROM and outputs the program and data to the RAM 1002 or the external storage 1007.

An I/F 1009 includes a digital input/output port such as an analog video port or IEEE 1394, and an Ethernet port for outputting various items of information to the outside. Data input through these ports is taken into the RAM 1002 via the I/F 1009. Part of the function of the data obtaining unit 110 is realized by the I/F 1009.

The above-described elements are connected to one another by a bus 1010.

Figure 3A:
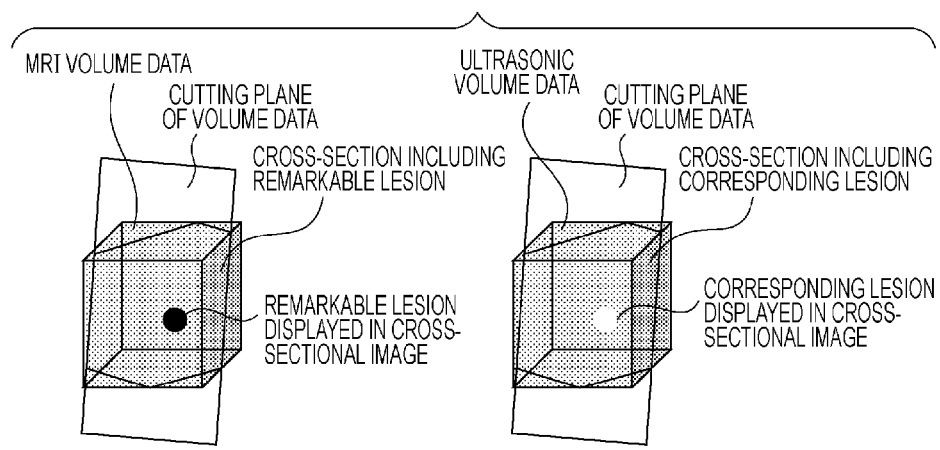
FIG. 3A is a diagram illustrating the overview of a process executed by the image processing apparatus.
Figure 3B:
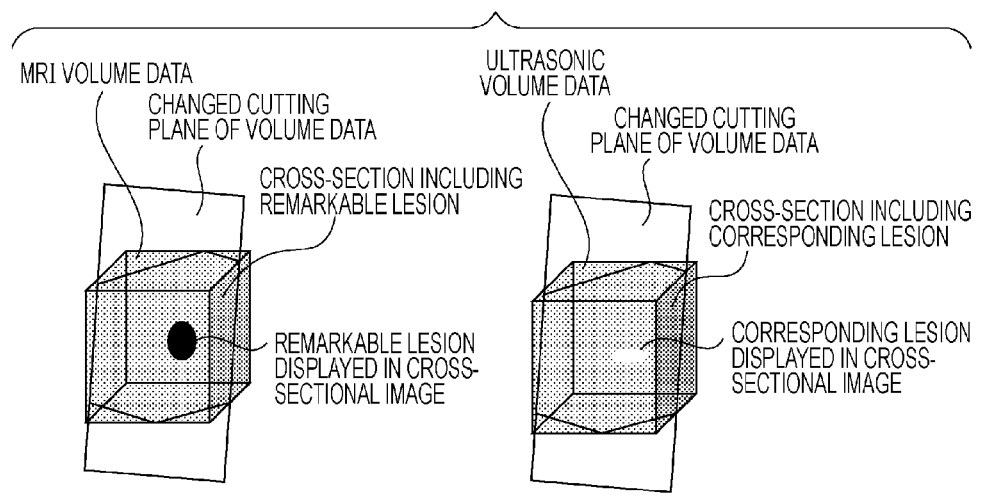
FIG. 3B is a diagram illustrating the overview of a process executed by the image processing apparatus.

The overview of a process executed by the above-described image processing apparatus 100 is described in accordance with FIGS. 3A and 3B. FIG. 3A illustrates a first item of three-dimensional image data (volume data of MRI) obtained from the first medical image collecting apparatus 170 and a second item of three-dimensional image data (volume data of an ultrasonic image) obtained from the second medical image collecting apparatus 180. These items of three-dimensional image data are items of three-dimensional image data to be aligned. Also, a plane (cutting plane) that passes through each of these items of volume data and a cross-section based on that plane are illustrated. Two-dimensional images of the cross-sections of these items of volume data are subjected to display processing performed by the image processing apparatus 100. Further, lesions displayed in the images of these cross-sections are illustrated. It is assumed that, in these items of volume data, the positions of portions regarded as these lesions are designated as designation points by the lesion designating unit 120. In the individual images, the lesions are indicated in different colors. This indicates that, even when images of the same subject are captured using MRI and ultrasound, the same subject appears different in these images.

In this circumstance, the planes that pass through the items of volume data are rotated by L degrees with respect to rotation axes that are straight lines that pass through the designation points in the same direction (e.g., X-axis direction). In this case, the planes are cooperatively rotated. Rotation parameters in this case (the direction of the rotation axes and the rotation angle L) are determined in accordance with the displacement or speed of a mouse. As illustrated in FIG. 3B, the cross-sectional-image generating unit 150 generates cross-sectional images defined by the rotated planes, and the display control unit 160 displays these cross-sectional images. Since the planes are rotated with respect to the straight lines that pass through the positions of the designation points as the rotation axes, the designation points are included in the cross-sectional images obtained after the rotation.

Even when the shapes of the corresponding lesions seem to match each other in the cross-sectional images in FIG. 3A, if the planes are cooperatively changed, as illustrated in FIG. 3B, the shapes of the lesions may be displayed as different shapes. Because a lesion is generally a three-dimensional body, even when shapes seen from one direction match each other, displayed lesions do not necessarily indicate the same lesion. Whether positions designated by a user in items of three-dimensional image data accurately correspond to each other can be checked, by the user, by cooperatively changing planes that pass through these items of three-dimensional image data and displaying cross-sectional images thereof.

A process executed by the above-described image processing apparatus 100 will be described in accordance with the flowchart of FIG. 4. This process is executed by the units implemented by the dedicated circuits illustrated in FIG. 1. This process is a process cooperatively executed by a program that is software and hardware such as a CPU. When the process is realized using a program, it is assumed that program code in accordance with the flowchart is already loaded from, for example, the external storage 1007 to the RAM 1002 before the following process is performed.

In step S401, the data obtaining unit 110 in the image processing apparatus 100 obtains groups of tomographic images generated by the first medical image collecting apparatus 170 and the second medical image collecting apparatus 180. Here, the data obtaining unit 110 obtains a group of MRI tomographic images and a group of ultrasonic tomographic images that are to be aligned.

In step S402, the data obtaining unit 110 obtains imaging conditions from the data server 190 or the first medical image collecting apparatus 170 and the second medical image collecting apparatus 180. The imaging conditions include, for example, information of the position and posture of the three-dimensional sensor attached to the ultrasonic probe, information of imaging postures, or information of apparatuses used for capturing images. The information of the three-dimensional sensor is used to align the groups of tomographic images with respect to a patient. Also, the information of the imaging postures can be used to align the postures of the groups of tomographic images. The information of the apparatuses is used to obtain the scale (enlargement/reduction ratio) of the captured images afterwards.

In step S403, the data obtaining unit 110 generates items of three-dimensional volume data from the groups of tomographic images using a known method. The data obtaining unit 110 may not necessarily generate volume data; instead, the data obtaining unit 110 may receive volume data from the data server 190. In step S404, the data obtaining unit 110 rotates and enlarges/reduces the groups of tomographic images based on the obtained imaging conditions, and adjusts the postures and sizes to match each other. Accordingly, a user does not need to manually perform these operations, resulting in a reduction of the user's labor. Also, the generated two items of volume data are described in the common reference coordinate system. Thus, the positions of lesions in the two items of volume data roughly match each other, excluding the influence of an error of the three-dimensional sensor and deformation of the subject. When the reference coordinate system is set in advance and steps S403 and S404 are simultaneously executed, the overall processing time can be reduced.

However, a human body includes relatively flexible tissues. The shape, position, and size of a lesion greatly change in accordance with the imaging date or the imaging posture. It is difficult to precisely align these images using image analysis. In such a case, the reliability is higher when the user manually aligns the images while looking at the images.

The process hereinafter is a process for supporting the manual operation of associating lesions.

In step S405, the display control unit 160 displays tomographic images on a screen. Tomographic images to be displayed may be arbitrarily selected from the groups of tomographic images and may be selectively displayed in accordance with a user operation of the mouse 1005 or the like. Operating the mouse 1005 or the like, the user selects tomographic images that are regarded to include a remarkable lesion and a corresponding lesion from the groups of MRI and ultrasonic tomographic images, and causes the selected tomographic images to be displayed. On the displayed tomographic images, the user inputs designations of the positions of portions regarded as the remarkable lesion and the corresponding lesion as first and second designation points. In accordance with this input, the lesion designating unit 120 obtains the positions of the first and second designation points in the reference coordinate system using the positions and postures of the tomographic images. The first designation point is a designation point in the first item of three-dimensional image data. The second designation point is a designation point in the second item of three-dimensional image data.

The first designation point is designated in the following steps. First, in accordance with an instruction input by the user, the display control unit 160 switches and displays an MRI tomographic image on the display unit 200. When a portion regarded as a remarkable lesion is included in the tomographic image, the user clicks, with the mouse 1005, the position of the portion regarded as the remarkable lesion on the display screen, thereby obtaining the position of the designation point in the reference coordinate system. Similarly, the second designation point is designated in the following steps. First, in accordance with an instruction input by the user, the display control unit 160 switches and displays an ultrasonic tomographic image on the display unit 200. When a portion regarded as a corresponding lesion is included in the tomographic image, the user clicks, with the mouse 1005, the position thereof, thereby designating the position.

In step S406, the cutting-surface changing unit 130 determines or changes cutting surfaces. When the process has proceeded to this step from step S405, the cutting-surface changing unit 130 determines, in each of the items of volume data, a plane that includes the designation point and whose posture is the initial posture (e.g., roll=0, pitch=0, yaw=0) as a cutting surface. In contrast, when the process has proceeded to this step from step S409 described later, the cutting-surface changing unit 130 determines a new cutting surface, using the following process, based on the cutting surface of each of the items of volume data after processing in step S406 has been executed at a prior time. That is, the cutting-surface changing unit 130 calculates new cutting surfaces by applying rotation transform to the cutting surfaces around the designation points (at a prior time) based on the rotation parameters obtained in step S409.

When there are two items of volume data of a breast of the same subject with different imaging postures, deformation based on the imaging postures is estimated using a known method, and that deformation is taken into consideration. Specifically, the degrees of changing the cutting surfaces of the two items of volume data are made different, taking the deformation into consideration. When there is deformation as such, the cutting surfaces are changed, taking the deformation into consideration. Accordingly, more accurate alignment can be supported.

In step S407, the cross-sectional-image generating unit 150 obtains cross-sectional images of the items of volume data based on the cutting surfaces determined or changed by the cutting-surface changing unit 130. The display control unit 160 displays the cross-sectional images on the display unit 200. Looking at these two cross-sectional images, the user who is a diagnostician can check whether the positions of the designation points match the position of the lesion.

As a display example, for example, the first and second cross-sectional images are displayed on two regions of a single screen obtained by vertically or horizontally dividing the screen. Alternatively, the first and second cross-sectional images are displayed on two screens. Alternatively, the first and second cross-sectional images are rendered in different colors and are overlappingly displayed. Alternatively, only one of the first and second cross-sectional images is selected and displayed.

Figure 5A:
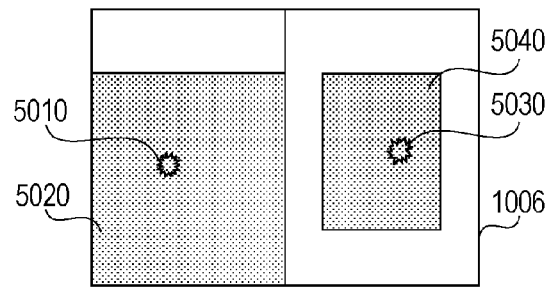
FIG. 5A is a diagram illustrating the overview of display as a result of processing performed by the image processing apparatus.
Figure 5B:
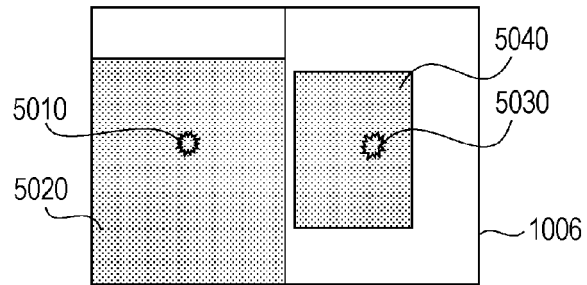
FIG. 5B is a diagram illustrating the overview of display as a result of processing performed by the image processing apparatus.
Figure 5C:
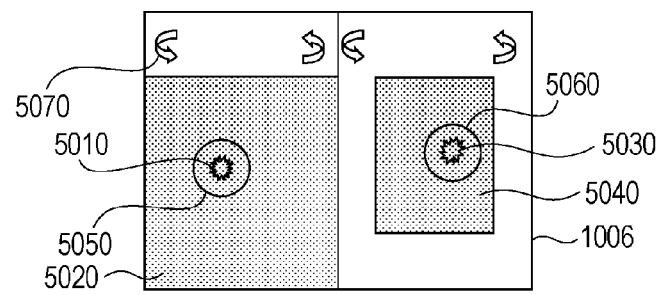
FIG. 5C is a diagram illustrating the overview of display as a result of processing performed by the image processing apparatus.

FIG. 5A illustrates an example of display of a first cross-sectional image 5020 including a remarkable lesion 5010 and a second cross-sectional image 5040 including a corresponding lesion 5030. Here, one screen is vertically divided into two screen regions, and the cross-sectional image 5020 and the second cross-sectional image 5040 are displayed horizontally next to each other. Strictly speaking, the remarkable lesion 5010 in FIGS. 5A to 5C is a first designation point indicating a portion regarded as a remarkable lesion designated by a user. Here, in order to simplify the description, this is called a remarkable lesion. Similarly, the corresponding lesion 5030 in FIGS. 5A to 5C is a second designation point indicating a portion regarded as a corresponding lesion designated by a user. Here, in order to simplify the description, this is called a corresponding lesion. As illustrated in FIG. 5B, the cross-sectional image 5020 and the second cross-sectional image 5040 are translated and displayed so that the positions of the remarkable lesion 5010 and the corresponding lesion 5030 become the center of the two screen regions. Accordingly, comparison of the remarkable lesion and the corresponding lesion becomes easier.

In other examples, graphic patterns such as cross shapes, squares, or circles indicating the positions of the remarkable lesion and the corresponding lesion are overlappingly displayed on the first and second cross-sectional images. Also, graphic patterns such as arrows visually indicating the rotation directions of cross-sections are displayed. Also, one of two items of volume data is volume-rendered, and, on this item of volume data, a graphic pattern such as a plane indicating the position and posture of the other cross-sectional image is overlappingly rendered. Also, whether to overlap various graphic patterns can be selected, and the selected graphic patterns are displayed. FIG. 5C illustrates an example where a circle 5050 indicating the position of the remarkable lesion, a circle 5060 indicating the position of the corresponding lesion, and an arrow 5070 indicating the rotation direction are overlappingly displayed.

When the user wishes to change the cutting surfaces and continue checking, the user inputs such an instruction using a mouse or the like. The change operation unit 140 receives this input (YES in step S408), and obtains rotation parameters (the direction of the rotation axis and the rotation angle L) for cooperatively changing the cutting surfaces in accordance with the input (step S409). The parameters are obtained after a mouse operation is obtained. The rotation angle and the direction of the rotation axis are obtained from the position, the amount of movement, and the movement direction of the mouse while a button is being pressed.

As an embodiment of changing the cutting surfaces in accordance with an input using the mouse, for example, the first or second cross-sectional image displayed on the display unit 200 is selected using the mouse 1005. Thereafter, the mouse 1005 is dragged while a button of the mouse 1005 is continuously pressed, thereby calculating rotation parameters that will rotate the cross-section in a direction in which the dragging operation is performed. At that time, the direction of the rotation axis may be calculated in accordance with the movement direction of the mouse 1005 at the time the mouse 1005 is dragged, and the rotation angle may be calculated in accordance with the amount of movement of the mouse 1005 at the time the mouse 1005 is dragged. For example, displacement of the mouse 1005 serves as a two-dimensional vector on the cross-sectional image, and a value in proportion to the magnitude of the vector serves as the rotation angle. A vector that is orthogonal to this vector on the cross-sectional image is set as the rotation axis. In another example, instead of dragging the mouse 1005, the user assigns rotation operations in individual directions and a change of the rotation angle to specific keys of a keyboard. Alternatively, operation buttons may be arranged on a display screen, and an operation is entered by clicking the operation buttons using the mouse.

When the user who sees the cross-sectional images displayed in step S407 determines that the designation points do not correspond to each other, the user enters an input to re-designate designation points using the mouse or the like. The change operation unit 140 receives this input (YES in step S410) and re-designates the designation points (step S411). The user observes the first and second cross-sectional images, and multilaterally evaluates the degree of similarity such as the shape of the lesion or the appearance of a surrounding portion. Accordingly, the user can accurately re-designate the position of the remarkable lesion or the corresponding lesion.

When the user determines, based on the cross-sectional images displayed in step S407, that the alignment of the lesions is completed, the user inputs an instruction to terminate the alignment. The change operation unit 140 receives this input (YES in step S412), and the image processing apparatus 100 stores the designation points at that time as corresponding points in the two items of volume data in a storage unit (not illustrated). Further, the display control unit 160 outputs information of the corresponding designation points to the display unit 200 (step S413), and displays the information on the display unit 200.

When no instruction to change the cutting surfaces or to re-designate the designation points is input (NO in step S408 or NO in step S410), the flow enters stand-by until an instruction to terminate the alignment is input, and, when such an instruction is input, this input is accepted.

As described above, according to the image processing apparatus according to the first embodiment, the position of a portion regarded as a remarkable lesion in one of two items of three-dimensional image data (first designation point) and the position of a portion regarded as a corresponding lesion in the other three-dimensional image data (second designation point) can be designated. Cross-sections with the same posture including the individual designation points can be generated from the items of three-dimensional image data and displayed. At that time, the positions of the designation points can be corrected, as occasion calls, on cross-sectional images seen from various directions. In this way, the positions of the lesions can be more accurately designated. As a result, cross-sectional images including the individual designation points are observed from various directions, and the degree of similarity such as the shape of the lesion or the appearance of a surrounding portion is multilaterally evaluated, thereby efficiently performing an operation of identifying the lesion.

By cooperatively rotating the cross-sections, the user is prompted to compare features of images and further to compare changes of the features. The postures of two groups of tomographic images are aligned based on imaging conditions, and features of the images are cooperatively changed, thereby prompting the user to perform alignment. As a whole, alignment that has high reliability and that places less burden on the user can be realized.

First Modification of First Embodiment

In the first embodiment, the case where the first cross-sectional image including the remarkable lesion and the second cross-sectional image including the corresponding lesion are cooperatively rotated has been described. That is, the method effective in the case where the posture of the first cross-sectional image and the posture of the second cross-sectional image match each other from the beginning has been described. In this modification, the individual images are not only cooperatively rotated, but also independently rotated. For example, only the second cross-sectional image may be rotated while the first cross-sectional image is fixed, or only the first cross-sectional image may be rotated while the second cross-sectional image is fixed. For example, by performing a dragging operation while the left button of the mouse is being pressed, only the first cross-sectional image can be rotated in a direction in which the dragging operation is performed. Similarly, by performing a dragging operation while the right button of the mouse is being pressed, only the second cross-sectional image can be rotated in a direction in which the dragging operation is performed. By performing a dragging operation while the left and right buttons of the mouse are being pressed, the first and second cross-sectional images can be cooperatively rotated in a direction in which the dragging operation is performed.

As described above, when the posture of the first cross-sectional image and the posture of the second cross-sectional image do not match each other, the postures of the first and second cross-sectional images can be adjusted to match each other by rotating only one of the first and second cross-sectional images.

In another example, when the cross-sectional images are cooperatively rotated, there is provided a mode in which the amount of rotation of one of the cross-sectional images is increased to be greater than that of the other cross-sectional image in accordance with an input. When a rotation instruction is given using the mouse, one of the cross-sectional images is more greatly rotated than the other cross-sectional image. Accordingly, the positions and postures of the two cross-sectional images can be adjusted to match each other. In particular, compared with the case where one of the cross-sectional images is made still, the user can compare changes of image information of the cross-sectional images in accordance with rotation. Accordingly, the user can efficiently perform precise alignment.

Second Modification of First Embodiment

In the first embodiment, in step S405, the positions of the remarkable lesion and the corresponding lesions are individually and manually designated. In a second modification, this is omitted, and the position of the remarkable lesion obtained in step S405 is set as the initial position (rough position) of the corresponding lesion. Also, a process of computing candidates for the position of the corresponding lesion by searching the vicinity of the initial position set above is executed. In this case, for example, a volume of a certain size with the remarkable lesion as the center (e.g. 5*5*5 voxels) is cut out from the first volume data and used as a template. Regions similar to this template are obtained from the second volume data using a known pattern matching technique.

Here, when there are multiple lesions in a subject, there may be cases where the corresponding lesion which corresponds to the remarkable lesion is not accurately calculated. However, according to the present embodiment, the user can accurately re-designate the position of the corresponding lesion while referring to the displayed individual cross-sectional images. Accordingly, the user's effort of designating the corresponding lesion can be saved by automatically computing the initial position of the corresponding lesion.

Third Modification of First Embodiment

In the first embodiment, the case where one corresponding lesion which corresponds to one remarkable lesion is designated has been described by way of example. However, the number of lesions to be designated is not limited to this. For example, when there are multiple lesions in a subject, multiple corresponding lesions which correspond to multiple remarkable lesions are individually designated. In this case, for example, two remarkable lesions and their corresponding lesions are selected from among the multiple lesions, and the first and second cross-sectional images are cooperatively rotated around rotation axes, namely, a straight line that connects the two remarkable lesions and a straight line that connects the two corresponding lesions. Accordingly, while the relationship between the two lesions is being checked, the two corresponding lesions which correspond to the two remarkable lesions can be more accurately designated. By repeating a process of selecting two remarkable lesions from among the multiple lesions and a process of designating two corresponding lesions which correspond to the two remarkable lesions, multiple corresponding lesions which correspond to multiple remarkable lesions can be more accurately designated.

Fourth Modification of First Embodiment

In the first embodiment, the case where a group of tomographic images obtained by capturing images of a subject beforehand using an MRI apparatus or an X-ray CT apparatus is used as the first three-dimensional image data has been described. Also, the case where a group of tomographic images obtained by capturing images of the subject beforehand using an ultrasonic image diagnosis apparatus is used as the second three-dimensional image data has been described. However, the three-dimensional image data used is not limited to these images. In this modification, groups of tomographic images obtained by capturing images of a subject at different times (dates and times) using the same modality (namely, items of data over time) are used as first and second items of three-dimensional image data. Alternatively, groups of tomographic images obtained by capturing images of a subject with different imaging postures (e.g., the subject lays on his/her back and on his/her face) using the same modality are used as first and second items of three-dimensional image data.

Here, volume data is not reconstructed in advance from the groups of tomographic images. Instead, using a known method, cross-sectional images are directly generated from the groups of tomographic images. Alternatively, volume data directly obtained in advance using a three-dimensional ultrasonic probe is used.

Fifth Modification of First Embodiment

In the first embodiment, a cross-sectional image of three-dimensional image data is generated based on a cutting surface determined by the cutting-surface changing unit 130. However, generation of a cross-sectional image is not limited to this. In this modification, volume data is subjected to image processing to generate new volume data where how a subject appears is adjusted, and the cross-section of the new volume data is generated as a cross-sectional image. Image processing such as edge enhancement processing and pseudo-color processing based on organ segmentation results is applied to volume data to generate new volume data, and a cross-sectional image thereof is generated. Alternatively, using a known method, a process of converting an MRI image into an image captured as if using an ultrasonic image diagnosis apparatus is applied to volume data to generate new volume data, and a cross-sectional image thereof is generated. After a cross-sectional image is generated from the new volume data, image processing described above is applied to the cross-sectional image.

As long as an image is generated from three-dimensional image data based on a calculated cross-section, a generated cross-sectional image may not necessarily be an image that visualizes voxel values of the cross-section. In this modification, after a certain range in a normal direction around the cross-section is set, a projected image obtained by computing, for each point of the cross-section, the maximum value of voxel values in the normal direction within that range is used as a cross-sectional image.

Sixth Modification of First Embodiment

In the first embodiment, the case where two items of three-dimensional image data are used has been described. The technique described in the present embodiment is applicable to the case where three or more items of three-dimensional image data are used. In this modification, corresponding lesions which correspond to a remarkable lesion are individually designated. In another example, a user repeats designating lesions while comparing three or more lesions.

Seventh Modification of First Embodiment

In a seventh modification, in addition to processing performed by the display control unit 160 in the first embodiment, the two cross-sectional images are cooperatively enlarged or reduced. In accordance with an input of the enlargement or reduction ratio input by operating a mouse or a keyboard, the cross-sectional images are changed in accordance with the same enlargement or reduction ratio and re-displayed. Accordingly, small regions are enlarged and displayed, and more detailed examinations are performed, or large regions are displayed and the tendencies of the images are estimated. In such a manner, whether the images are aligned can be examined in a more detailed manner based on the displayed images.

Second Embodiment

In the present embodiment, the amounts of changing the cutting surfaces are reduced when the certainty of correspondence is improved. The certainty of correspondence is determined based on information input by a user, such as the number of times the designation points or the cutting surfaces are changed, or pattern matching of the images. The difference in the apparatus configuration and processing from the first embodiment will be mainly described.

Figure 6:
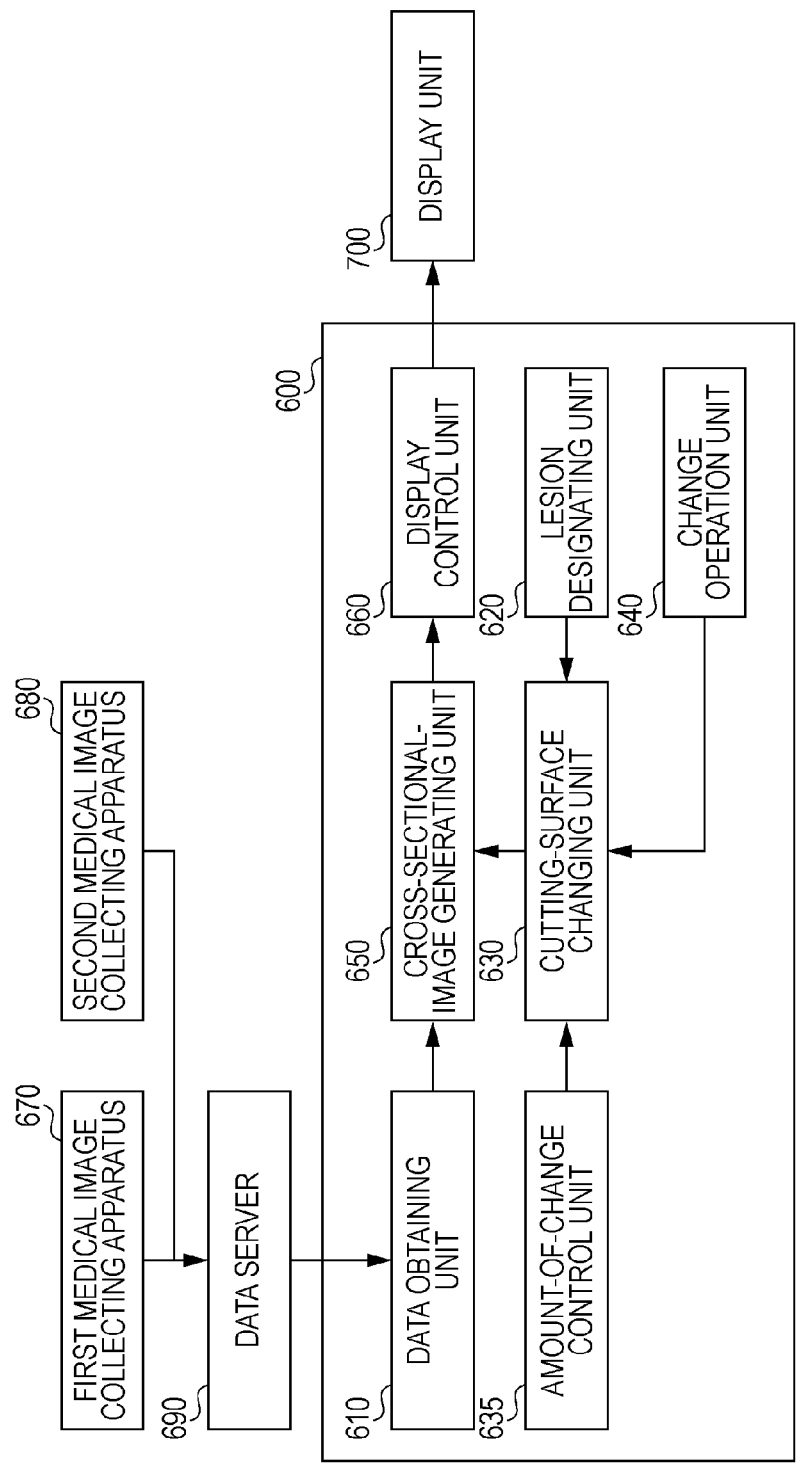
FIG. 6 is a block diagram of an image processing system according to a second embodiment.

FIG. 6 illustrates the configuration of an image processing system according to a second embodiment. Descriptions of portions overlapping with those of the first embodiment will be omitted.

An amount-of-change control unit 635 receives, as input, the first and second cross-sectional images that are output of a cross-sectional-image generating unit 650. Also, the amount-of-change control unit 635 receives, as input, the positions of the first and second designation points that are output of a lesion designating unit 620. The amount-of-change control unit 635 calculates the level of similarity of regions represented by the designation points, and outputs the level of similarity to a cutting-surface changing unit 630.

Regarding an embodiment of the level of similarity, the level of similarity is determined based on the number of times the user re-designates the designation points or the number of times the user changes the cross-sections. This is because, as the user repeats changing the designation points or the cross-sections, the probability that the corresponding designation points match each other is regarded to be high.

Based on the level of similarity obtained from the amount-of-change control unit 635, the cutting-surface changing unit 630 adjusts the rotation parameters applied to the cutting surfaces. For example, the cutting-surface changing unit 630 calculates a correction coefficient using the following equation:

$$r = \frac{1}{n+1} \quad \text{[Math. 1]}$$

Here, r is the correction coefficient, and n is the number of times the first designation point and/or the second designation point is designated. A value obtained by multiplying, of the rotation parameters obtained from a change operation unit 640, the rotation angle by the correction coefficient is used as the actual rotation angle. According to the above equation, the correction coefficient becomes 1 when the number of times the first designation point and/or the second designation point is designated is 0. Thus, the designated rotation angle is output as it is to the cross-sectional-image generating unit 650. In contrast, for example, the correction coefficient becomes 0.2 when the number of times the first designation point and/or the second designation point is designated is 4. Thus, ⅕ of the designated rotation angle is output to the cross-sectional-image generating unit 650. That is, as the level of similarity improves when designation of the remarkable lesion and/or the corresponding lesion is repeated, it can be controlled that the rotation angle becomes slow.

In another embodiment, the level of similarity is calculated by comparing pixel values near the first and second designation points. For example, using a known pattern matching technique, the level of similarity between a partial image of the cross-sectional image with a designated size (e.g., 20*20 pixels) around the first designation points and a partial image of the cross-sectional image with the same size around the second designation point is calculated as a value ranging from 0 to 1.

In another example, when the designation points are sequentially updated, the amount of rotation is reduced as the amount of changing the designation points becomes smaller. A history of the position of each designation point updated by the lesion designating unit 620 in accordance with a user input is stored, and the amount of rotation is reduced when the displacement between the designated positions becomes smaller. When the displacement between the designation points becomes smaller, it can be regarded that the user is performing detailed alignment. By reducing the amount of rotation, detailed changes of image information can be compared. In this way, detailed alignment can be supported.

In another example, the cutting-surface changing unit 630 changes the correction coefficient multiplied to the amount of changing the cutting surfaces of items of volume data (rotation angle) in accordance with the level of similarity obtained from the amount-of-change control unit 635. For example, the correction coefficient is reduced as the level of similarity becomes higher, thereby suppressing the amount of change. For example, the correction coefficient is calculated using the following equation:

$$r = \frac{1}{4c+1} \quad \text{[Math. 2]}$$

Here, r is the correction coefficient, and c is the level of similarity between the first and second cross-sectional images. According to the above equation, the correction coefficient becomes 1 when the level of similarity is 0. Thus, the designated rotation angle is used as it is by the cutting-surface changing unit 630. In contrast, the correction coefficient becomes 0.2 when the level of similarity is 1. Thus, ⅕ of the designated rotation angle is used by the cutting-surface changing unit 630. That is, as the level of similarity improves, the postures of the cross-sections can be controlled so that the rotation angle becomes slow.

Figure 7:
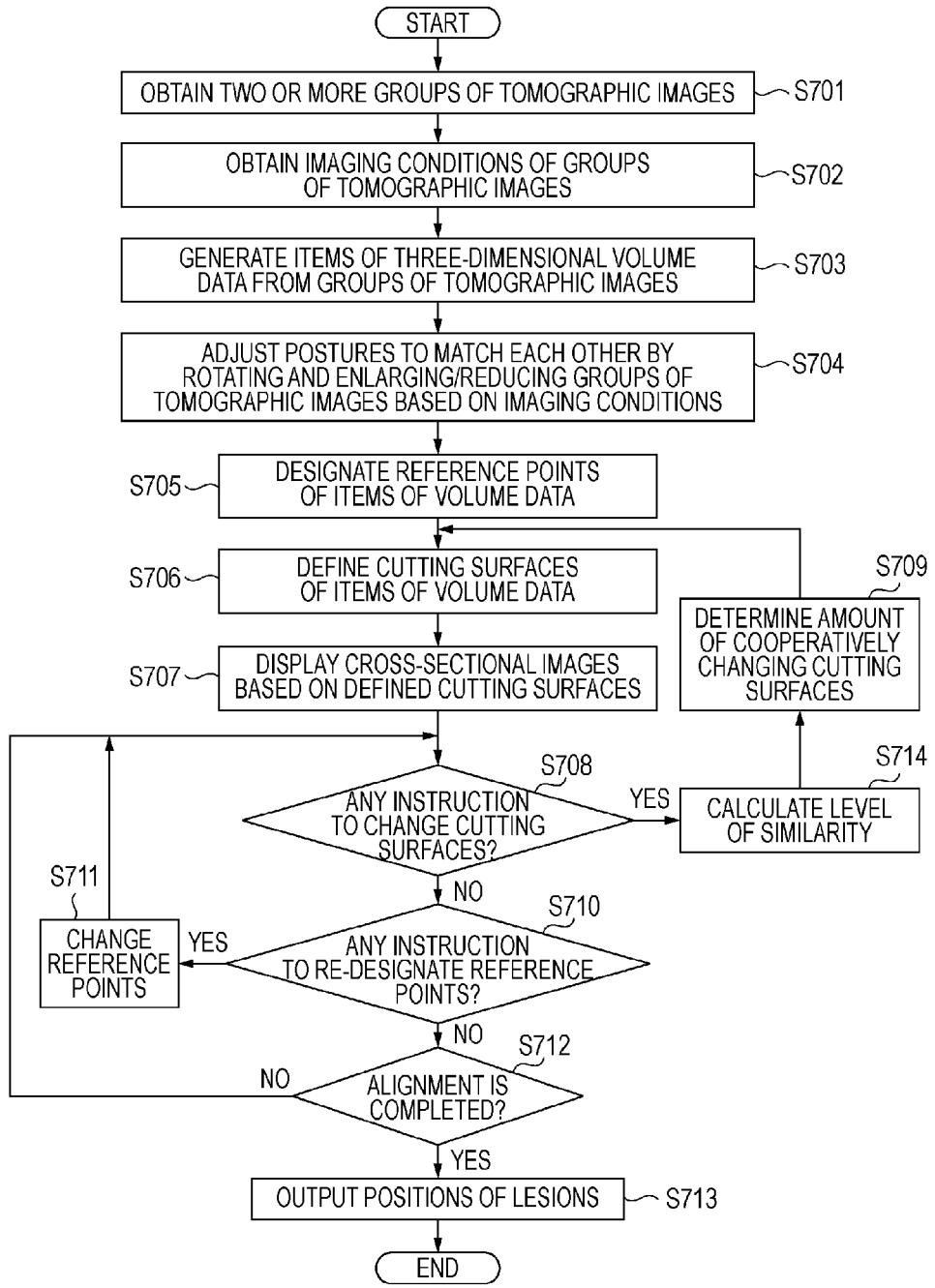
FIG. 7 is a flowchart illustrating the overview of a process executed by the image processing apparatus.

FIG. 7 illustrates the overview of a process executed by the image processing apparatus 100. Since processing from step S701 to step S708 and from step S710 to step S713 overlaps processing from step S401 to step S408 and from step S410 to step S413 in the first embodiment, descriptions thereof are omitted.

In step S714, the amount-of-change control unit 635 receives, as input, changes of the cutting surfaces and calculates the level of similarity.

In step S709, the cutting-surface changing unit 630 obtains the rotation parameters (the direction of the rotation axis and the rotation angle L) of the cutting surfaces from the change operation unit 640, and corrects the rotation angle based on the level of similarity.

Based on the rotation parameters determined in this manner, the cutting-surface changing unit 630 performs processing to cooperatively change the cutting surfaces (step S706).

By performing the foregoing process, the amounts of changing the cutting surfaces are suppressed as the accuracy of correspondence improves, and a diagnostician can easily perform more precise alignment.

First Modification of Second Embodiment

In the present embodiment, the correction coefficient of the rotation angle of the cross-sections is calculated based on the result of comparison between the cross-sectional image including the remarkable lesion and the cross-sectional image including the corresponding lesion. However, a method of controlling the method of generating cross-sectional images in accordance with the result of comparison between the cross-sectional image including the remarkable lesion and the cross-sectional image including the corresponding lesion is not limited to the above method. In this modification, the enlargement ratio of the first and second cross-sectional images is calculated. In this case, as part of processing in step S714, the amount-of-change control unit 635 obtains the level of similarity between lesions and calculates the enlargement ratio in accordance with the level of similarity. The enlargement ratio is calculated as a value in accordance with the level of similarity using, for example, the following equation:

$$Z = 2(c+1) \quad [\text{Math.3}]$$

Here, Z is the enlargement ratio, and c is the level of similarity between lesions. According to the above equation, the enlargement ratio becomes 1 when the level of similarity is 0, and the enlargement ratio becomes 4 when the level of similarity is 1.

Using the enlargement ratio calculated as above, display regions of the first and second cross-sectional images can be enlarged.

As above, as the level of similarity between the lesions improves, the remarkable lesion and the corresponding lesion can be enlarged and observed. Therefore, the remarkable lesion and/or the corresponding lesion can be more accurately designated.

Second Modification of Second Embodiment

In the present embodiment, the level of similarity between the cross-sectional image including the remarkable lesion and the cross-sectional image including the corresponding lesion is calculated. In a second modification, the level of similarity between items of volume data is calculated. For example, using mutual information amount by way of example, the level of similarity between partial volume data with a designated size (e.g., 20*20*20 voxels) around the remarkable lesion and partial volume data with the same size around the corresponding lesion is calculated as a value ranging from 0 to 1.

Other Embodiments

The present invention can take various embodiments such as a system, an apparatus, a method, a program, and a storage medium. Specifically, the present invention is applicable to a system including a plurality of devices and to an apparatus including a single device.

In the foregoing embodiments, at least some of the units illustrated in FIG. 1 (the data obtaining unit 110, the lesion designating unit 120, the cutting-surface changing unit 130, the change operation unit 140, the cross-sectional-image generating unit 150, and the display control unit 160) may be realized as independent apparatuses. In that case, the image processing system as a whole constitutes the present invention.

Alternatively, at least some of the units illustrated in FIG. 1 may be realized as software including a program that realizes the functions thereof by installing the program into one or more computers and executing the program using a CPU(s) of the computer(s). In that case, the program, a storage medium storing the program, and a computer or a system in which the program is installed constitute the present invention.

Also, the functions of the above embodiments may be realized by executing the read program using the computer. Also, the functions of the embodiments may be realized by cooperation with an OS or the like running on the computer based on instructions from the program. In that case, the OS or the like may execute part of or the entirety of the actual processing to realize the functions of the above embodiments.

The present invention is not limited to the above embodiments, and various changes and modifications can be made without departing from the spirit and scope of the invention. Therefore, to apprise the public of the scope of the present invention, the following claims are appended.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST

100 Image processing apparatus
110 Data obtaining unit
120 Lesion designating unit
130 Cutting-surface changing unit
140 Change operation unit
150 Cross-sectional-image generating unit
160 Display control unit

The invention claimed is:

1. A medical image processing apparatus comprising:
a designation unit configured to designate a first designation point in first three-dimensional image data and designate a second designation point in second three-dimensional image data different from the first three-dimensional image data;
an association unit configured to associate the first designation point designated in the first three-dimensional image data and the second designation point designated in the second three-dimensional image data;
a cross-sectional-image generating unit configured to generate, based on a first cutting plane including the first designation point associated by the association unit, a first cross-sectional image based on the first three-dimensional image data and generate, based on a second cutting plane including the second designation point associated with the association unit, a second cross-sectional image based on the second three-dimensional image data; and
a change unit configured to cooperatively rotate each of a of the first cutting plane in the first three-dimensional image data and a around the first designated designation point and the second cutting plane in the second three-dimensional image data around the second designated designation point;
wherein the cross-sectional-image generating unit generates, based on the first cutting plane and the second cutting plane rotated by the change unit, the first cross-sectional image based on the first three-dimensional image data and the second cross-sectional image based on the second three-dimensional image data.

2. A medical image processing apparatus comprising:
a designation unit configured to designate a first designation point in first three-dimensional image data and designate a second designation point in second three-dimensional image data different from the first three-dimensional image data;
an association unit configured to associate the first designation point designated in the first three-dimensional image data and the second designation point designated in the second three-dimensional image data;
a cross-sectional-image generating unit configured to generate, based on a first cutting plane including the first designation point associated by the association unit, a first cross-sectional image based on the first three-dimensional image data and generate, based on a second cutting plane including the second designation point associated with the association unit, a second cross-sectional image based on the second three-dimensional image data; and
a change unit configured to cooperatively rotate each of the first cutting plane in the first three-dimensional image data around the first designated point and the second cutting plane in the second three-dimensional image data around the designated designation point;
wherein the cross-sectional-image generating unit generates, based on the first cutting plane and the second cutting plane rotated by the change unit and an amount of change of the designation points designated by the designation unit, the first cross-sectional image based on the first three-dimensional image data and the second cross-sectional image based on the second three-dimensional image data.

3. A medical image processing apparatus comprising:
a designation unit configured to designate a first designation point in first three-dimensional image data and designate a second designation point in second three-dimensional image data different from the first three-dimensional image data obtained by capturing images of a subject using different methods;
an association unit configured to associate the first designation point designated in the first three-dimensional image data and the second designation point designated in the second three-dimensional image data;
a cross-sectional-image generating unit configured to generate, based on a cutting plane including the designation point associated by the association unit, a cross-sectional image based on the first three-dimensional image data and generate, based on a second cutting plane including the second designation point associated with the association unit, a second cross-sectional image based on the second three-dimensional image data; and
a change unit configured to cooperatively rotate each of the first cutting plane in the first three-dimensional image data around the first designated designation point and the second cutting plane in the second three-dimensional image data around the second designated designation point;
wherein the cross-sectional-image generating unit generates, based on the first cutting plane and the second cutting plane rotated by the change unit, the first cross-sectional image based on the first three-dimensional image data and the second cross-sectional image based on the second three-dimensional image data with a level of similarity between subjects in the cross-sectional images.

4. The medical image processing apparatus according to claim 1, wherein the designation points of three-dimensional image data are designation points of image data obtained by capturing images of a subject using different methods, and wherein the medical image processing apparatus further comprises an adjustment unit configured to align a posture of the subject captured in the designation points of three-dimensional image data based on an imaging condition at a time of image capturing.

5. A medical image processing apparatus comprising:
a designation unit configured to designate a first designation point in first three-dimensional image data and designate a second designation point in second three-dimensional image data different from the first three-dimensional image data obtained by capturing images of a subject using different methods;
an association unit configured to associate the first designation point designated in the first three-dimensional image data and the second designation point designated in the second three-dimensional image data;
a cross-sectional-image generating unit configured to generate, based on a first cutting plane including the first designation point associated by the association unit, a first cross-sectional image based on the first three-dimensional image data and generate, based on a second cutting plane including the second designation point associated with the association unit, a second cross-sectional image based on the second three-dimensional image data; and
a change unit configured to cooperatively rotate each of the first cutting plane in the first three-dimensional image data around the first designated designation point and the second cutting plane in the second three-dimensional image data around the second designated designation point;
wherein the cross-sectional-image generating unit generates, based on the first cutting plane and the second cutting plane rotated by the change unit, the first cross-sectional image based on the first three-dimensional image data and the second cross-sectional image based on the second three-dimensional image data, and cooperatively enlarges or reduces the cross-sectional images in accordance with at least one of a number of designations performed by the designation unit, a number of times displayed cross-sectional images are changed, and displacement of designation points designated by the designation unit.

6. The medical image processing apparatus according to claim 1, wherein each of the designation points of three-dimensional image data is a group of tomographic images obtained by capturing images of a subject, and
wherein the cross-sectional-image generating unit generates at least one of the tomographic images constituting the group of tomographic images.

7. The medical image processing apparatus according to claim 1, wherein the designation points of three-dimensional image data are designation points of three-dimensional image data obtained by capturing images of a same target using different methods.

8. The medical image processing apparatus according to claim 7, wherein the designation points of three-dimensional image data are designation points of three-dimensional image data obtained by capturing images of a subject with different imaging postures.

9. The medical image processing apparatus according to claim 7, wherein image capturing using the different methods is image capturing using any two of an X-ray CT imaging apparatus, an MRI imaging apparatus, and an ultrasonic imaging apparatus.

10. A medical image processing method comprising:
a step of designating a first designation point in first three-dimensional image data and designate a second designation point in second three-dimensional image data;
a step of associating the first designation point designated in the first three-dimensional image data and the second designation point designated in the second three-dimensional image data;
a step of generating, based on a cutting plane including the first designation point associated by the association unit, a first cross-sectional image based on the first three-dimensional image data and generate, based on a second cutting plane including the second designated designation point associated with the association unit, a second cross-sectional image based on the second three-dimensional image data; and
a step of cooperatively rotating each of the first cutting plane in the first three-dimensional image data around the first designated designation point and the second cutting plane in the second three-dimensional image data around the second designated designation point;
wherein, in the step of cooperatively rotating, based on the rotated first cutting plane and the second cutting plane, the first cross-sectional image based on the first three-dimensional image data and the second cross-sectional image based on the second three-dimensional image data are generated.

11. A medical image processing system comprising:
an obtaining unit configured to obtain first three-dimensional image data and second three-dimensional image data obtained by a plurality of imaging units;
a designation unit configured to designate a first designation point in the first three-dimensional image data and designate a second designation point in the second three-dimensional image data;
an association unit configured to associate the first designation point designated in the first three-dimensional image data and the second designation point designated in the second three-dimensional image data;
a cross-sectional-image generating unit configured to generate, based on a first cutting plane including the first designation point associated by the association unit, a first cross-sectional image based on the first three-dimensional image data and generate, based on a second cutting plane including the second designation point associated by the association unit, a second cross-sectional image based on the second three-dimensional image data; and
a change unit configured to cooperatively change each of the first cutting plane in the first three-dimensional image data and the second cutting plane in the second three-dimensional image data around the designated designation point,
wherein the cross-sectional-image generating unit generates, based on the first cutting plane and the second cutting rotated by the change unit, the first cross-sectional image based on the first three-dimensional image data and the second cross-sectional image based on the second three-dimensional image data.

12. A non-transitory storage medium storing a program causing a computer to execute:
a process of designating a first designation point in first three-dimensional image data and designate a second designation point in second three-dimensional image data;
a process of associating the first designation point designated in the first three-dimensional image data and the second designation point designated in the second three-dimensional image data;
a process of generating, based on a first cutting plane including the first designation point associated by the process of associating, a first cross-sectional image based on the first three-dimensional image data and generate, based on a second cutting plane including the second designation point associated by the process of associating, a second cross-sectional image based on the second three-dimensional image data;
a process of cooperatively changing each of the first cutting plane in the first three-dimensional image data around the first designated point and the second cutting plane in the second three-dimensional image data around the designated designation point; and
a process of generating data for displaying, on a display unit, the first and second cross-sectional images of the first and second designation points of three-dimensional image data,
wherein, in the cooperatively rotating process, based on the rotated cutting planes, the first cross-sectional image based on the first three-dimensional image data and the second cross-sectional image based on the second three-dimensional image data are generated.

13. The medical image processing apparatus according to claim 1, wherein the change unit decreases an angle of rotation corresponding to generation of cross-sectional images in accordance with an increase of one of a number of times designations are performed by the designation unit and a number of times the cross-sectional images are generated.

14. The medical image processing apparatus according to claim 2, wherein the change unit decreases an angle of the rotation corresponding to generation of cross-sectional images in accordance with an increase of one of a number of times designations are performed by the designation unit and a number of times the cross-sectional images are generated.

15. The medical image processing apparatus according to claim 3, wherein the change unit decreases an angle of the rotation corresponding to generation of cross-sectional images in accordance with an increase of one of a number of times designations are performed by the designation unit and a number of times the cross-sectional images are generated.

16. The medical image processing apparatus according to claim 1, wherein the designation unit re-designates the designation point on the cross-sectional image based on the first three-dimensional image data or the cross-sectional image based on the second three-dimensional image data after the cross-sectional image based on the first three-dimensional image data and the cross-sectional image based on the second three-dimensional image data are generated based on the cutting planes rotated by the change unit.

17. The medical image processing apparatus according to claim 1, wherein the designation unit re-designates the first designation point on the first cross sectional image based on the first three dimensional image data, and wherein the change unit rotates the first cutting plane in the first three-dimensional image data around the re-designated first designation point and the second cutting plane in the second three dimensional image data around the second designated designation point.

* * * * *